United States Patent [19]
Bentz

[11] 4,132,944
[45] Jan. 2, 1979

[54] APPARATUS FOR MONITORING ELECTRICAL PROPERTIES OF A LIQUID

[75] Inventor: Allan J. Bentz, Norwich, N.Y.

[73] Assignee: Simmonds Precision Products, Inc., Tarrytown, N.Y.

[21] Appl. No.: 857,347

[22] Filed: Dec. 2, 1977

Related U.S. Application Data

[63] Continuation of Ser. No. 730,616, Oct. 7, 1976, abandoned.

[51] Int. Cl.² ........................................... G01N 27/42
[52] U.S. Cl. ..................................... 324/30 R; 324/29
[58] Field of Search ................. 324/60 C, 61 R, 65 R, 324/29, 30 R, 30 B

[56] References Cited
U.S. PATENT DOCUMENTS 3,867,687  2/1975  Gealt .................................. 324/30 R Primary Examiner—M. Tokar
Attorney, Agent, or Firm—Edwin E. Greigg

[57] ABSTRACT

Apparatus for monitoring the temperature, and the electrical conductance and capacitance, of a liquid product during processing of the liquid product, and automatically converting the measured electrical conductance and capacitance values to the conductance capacitance of the liquid product at a selected reference temperature of the product. An a.c. sine wave voltage is applied across a conductivity cell immersed in the liquid and an admittance signal proportional to the current flowing through the cell is resolved into a signal proportional to the conductance of the liquid, and a signal proportional to the capacitance of the liquid, within the cell. A thermocouple at the conductivity cell produces a signal proportional to the liquid temperature, which is compared with a selected reference temperature signal, and the signal proportional to the difference between the temperature signal and the reference signal is applied to temperature compensation circuits to produce respective signals proportional to the conductance and capacitance of the liquid at the selected reference temperature.

7 Claims, 2 Drawing Figures

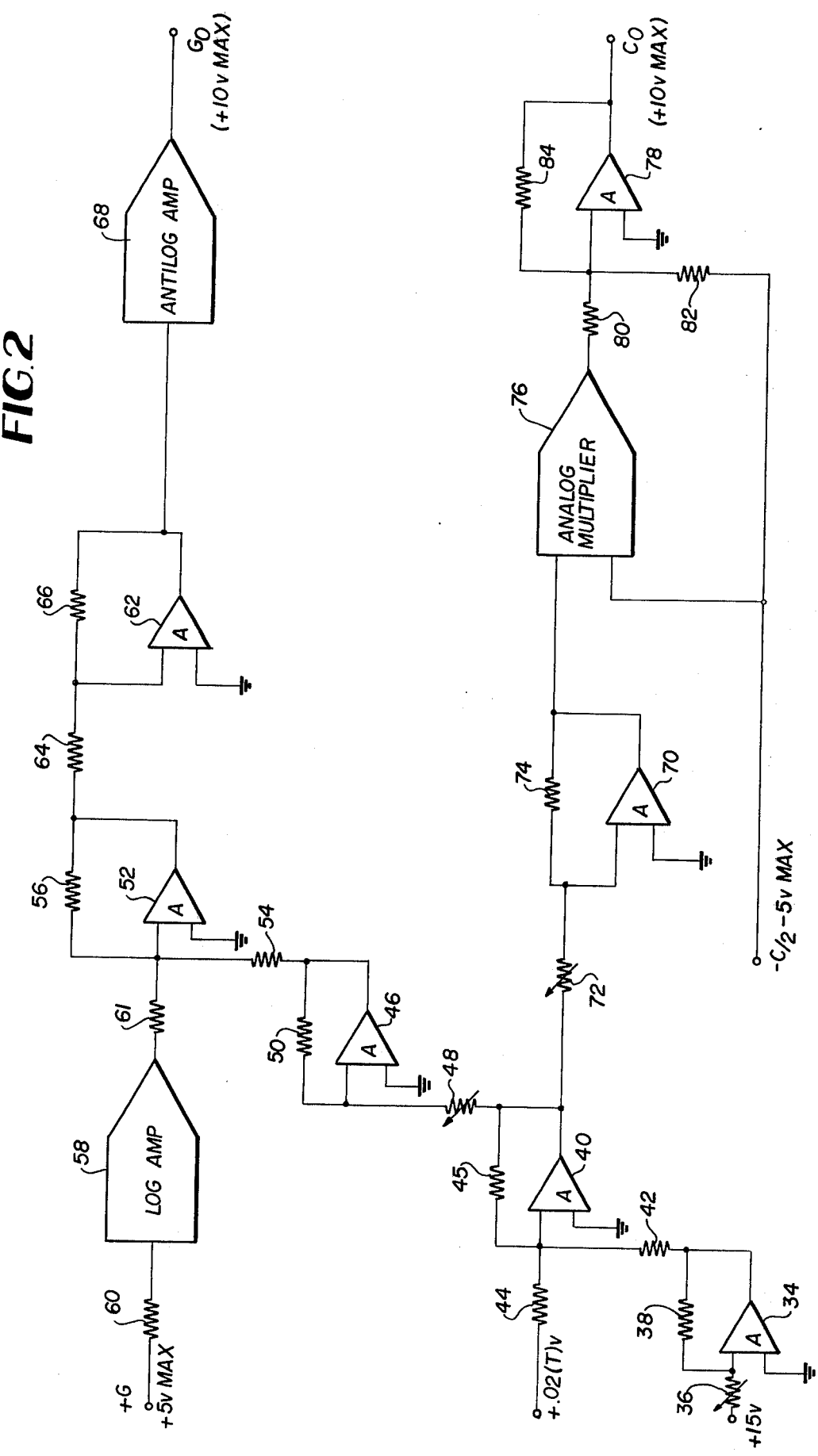

APPARATUS FOR MONITORING ELECTRICAL PROPERTIES OF A LIQUID

This is a continuation, of application Serial No. 730,616, filed Oct. 7, 1976, now abandoned.

BACKGROUND OF THE INVENTION

1. Field of the Invention

The invention relates generally to the measurement of electrical characteristics of a liquid, and in particular, to the continuous monitoring of the electrical conductance and/or capacitance of a liquid product during a chemical processing of the liquid, and the automatic conversion of the characteristics measured to the value of these characteristics at a selected reference temperature of the liquid product.

2. Description of the Prior Art

During chemical processing employing nonaqueous liquids, such as alcohols, ketones, organic acids and other hydrocarbon liquid products produced by the petrochemical industry, it is desirable to continuously monitor the liquid during the processing operation to assure control of the process and determine its endpoint. Where one or more of the electrical properties of the liquid changes in value during the processing operation, the end point of the process can be determined by continuously monitoring one or more of these electrical properties of the liquid product. For example, U.S. Pat. Nos. 3,779,892 and 3,868,315, issued Dec. 18, 1973 and Feb. 25, 1975, respectively, to Eric O. Forster et al., disclose an electronic measuring technique for continuously measuring the difference between the electrical resistance (and capacitance) of asphalt during an oxidation process and a reference standard having a resistance (and capacitance) corresponding to the finished product, to stop the process when the asphalt being oxidized has the same resistance as the reference standard. However, since both the resistance and capacitance of a liquid changes with the temperature, the measuring technique disclosed in U.S. Pat. No. 3,868,315 is restricted to a process in which the liquid product being monitored is maintained at a constant and uniform temperature for which the resistance and capacitance values of the reference standard apply. The equipment required to maintain a liquid product at a constant and uniform temperature during a chemical process can be very costly, especially if the only reason for such tight temperature control is for prompt and accurate shutdown of the process, as determined by the electrical characteristics of the liquid. Also, some processes may be more effective if the temperature of the liquid product is varied during the process.

OBJECT AND SUMMARY OF THE INVENTION

Therefore, it is a primary object of this invention to disclose an apparatus for monitoring the temperature, and the electrical conductance and/or capacitance of a liquid product while this liquid product is being processed, and automatically converting the measured conductance and capacitance values to the conductance and capacitance of the liquid product at a preselected reference temperature of the liquid.

It is also an object of the invention to disclose an apparatus for quickly and continuously determining the electrical conductance and/or capacitance of a liquid at a preselected reference temperature during chemical processing of the liquid, whose accuracy is essentially unaffected by variations in the processing temperature of the liquid within a preselected temperature range.

It is another object of the invention to disclose an apparatus for quickly and continuously determining the electrical capacitance of a liquid at a preselected reference temperature during chemical processing of the liquid, having a conductivity cell immersed in the liquid for sensing the electrical admittance of the liquid, in which the conductivity cell can be interchanged with any other conductivity cell having a different capacitance in air ($C'_o$), without changing any circuit values and still maintain a measurement accuracy within 1% over a process temperature range which changes the relative dielectric constant plus or minus 10%.

The liquid sensing probe of this apparatus consists of a conductivity cell which has an integrally mounted thermocouple. When the conductivity cell is connected across an a.c. sine wave excitation source, the resulting current is proportional to the cell admittance. This current is resolved into two orthogonal components: a charging current which leads the exitation voltage by 90° and is proportional to the dielectric constant (k) of the liquid between the electrodes of the conductivity cell, and an ohmic current which is in phase with the exitation voltage and is proportional to the reciprocal of the resistance, or conductance, of the liquid.

Temperature compensation for the real component of the admittance (conductance) is based on the Arrhenius absolute rate model. Accordingly, conductance is a function of the thermal energy (RT), and the activation energy $\Delta E^{\neq}$, which separates equilibrium positions of the conducting species. The conductance G at a process temperature T may be corrected to a conductance $G_o$ at the reference temperature $T_o$ by the equation:

$$G_o = G \, 10^{b(T_o-T)}$$

or, $$\mathrm{Log} \, G_o = \log G + b \, (T_o - T)$$

where:
$b = \Delta E^{\neq}/[2.303 \, R \, T_{ok}^2]$, in which
$\Delta E^{\neq}$ = activation energy in calories/mole
$R$ = the gas constant in calories/(mole ° K.), and
$T_{ok}$ = $T_o$ in degrees Kelvin The thermocouple embedded in the probe produces a signal proportional to the process liquid temperature T, while constant signals analogous to the reference temperature $T_o$ and to b are generated by appropriate circuitry. These analog signals proportional to T, $T_o$ and b, are combined to form a signal representing the expression $b(T_o - T)$. The log G function is generated from the signal representative of the conductance G, added to the signal representing $b \, (T_o - T)$, and sent to an antilog amplifier, whose output signal is representative of the desired conductance value $G_o$ of the liquid.

The imaginary component of the admittance when divided by the excitation frequency in radians per second is the capacitance C of the liquid at the processing temperature T. Based on the simple volume expansion for the liquid and the Debye model for dilute solutions of polar molecules, the temperature dependence of the dielectric constant k of the liquid takes the form $$k = k_o - \alpha(T - T_o),$$

as reported in the National Bureau of Standards circular 514. In terms of measured capacitance, $$C_o = C - aC(T_o - T),$$

where $C_o$ is the capacitance of the liquid at the reference temperature $T_o$, $K_o$ is the dielectric constant of the liquid at the reference temperature $T_o$, $\alpha$ is the volume expansion coefficient, and $a = \alpha/K_o$.

This equation assumes that the capacitance $C'_o$ of the cell in air at the reference temperature $T_o$ is approximately equal to the capacitance C of the liquid at the measured process temperature T divided by the dielectric constant k of the liquid at the process temperature T. This assumption was made to allow the use of different conductivity cells having different $C'_o$ values, without changing any of the circuit values, and is accurate so long as the dielectric constant variation with temperature is no more than plus or minus ten percent, which is the case for most applications in which this apparatus is used. For the exceptional process requiring monitoring over a wider temperature range, a specific conductivity cell can be used, and the constant $\alpha$ calculated for the $C'_o$ value of that conductivity cell.

A signal proportional to $a(T_o - T)$ is generated by the same method used to form the $b(T_o - T)$ term in the conductance compensation circuit. The signal proportional to the capacitance C of the liquid and the signal proportional to $a(T_o - T)$ are supplied to an analog multiplier which generates an a signal proportional to the product of these two signals, $aC(T_o - T)$. This product signal is then electrically subtracted from the capacitance signal C to produce a signal proportional to the capacitance $C_o$ of the liquid at the reference temperature $T_o$.

The invention will be better understood as well as other objects and advantages thereof become more apparent from the following detailed description of the invention taken in conjunction with the drawing.

BRIEF DESCRIPTION OF THE DRAWING

FIG. 2 is a schematic diagram of the temperature compensation circuits of a preferred embodiment of this invention, for determining the conductance and capacitance of the liquid at a selected reference temperature.

DESCRIPTION OF THE PREFERRED EMBODIMENT

Figure 1:
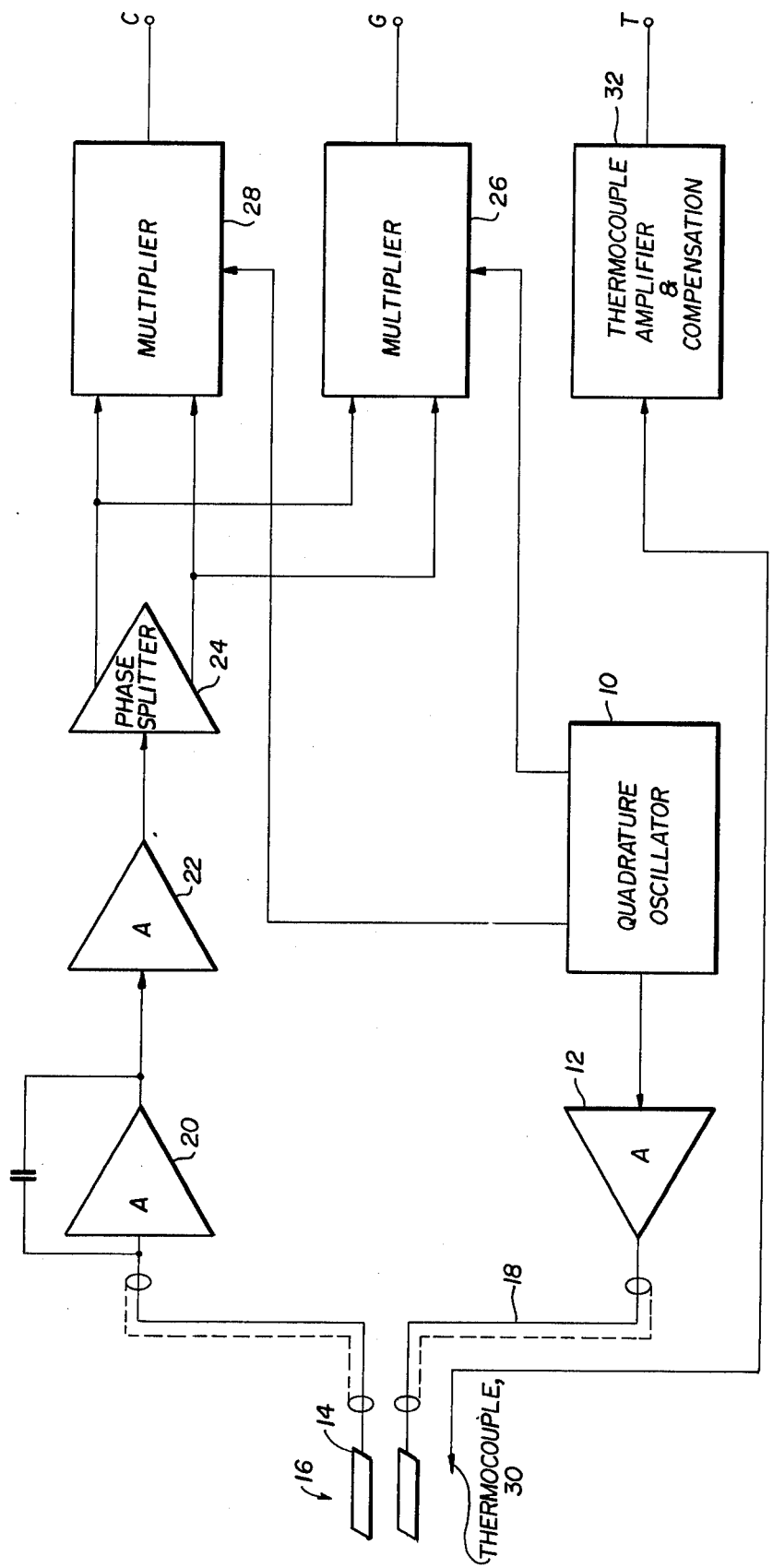
FIG. 1 is a schematic block diagram showing a preferred embodiment of this invention for monitoring the temperature, conductance, and capacitance of the liquid being processed.

Referring now to FIG. 1, a quadrature oscillator 10 generates a 1000 Hz sine wave voltage, which is amplified by an amplifier 12 and applied to a conductivity cell 14 of a liquid sensor probe 16 immersed in the liquid being processed through shielded lines 18. The current flowing through the conductivity cell 14 is converted into a proportional voltage by a current transducer 20, and amplified by a narrow band amplifier 22. This amplified voltage signal is then divided into two signals of opposite polarity by the phase splitter 24, which are supplied to respective circuits of a first multiplier 26 and a second multiplier 28.

In the first multiplier 26, the phase splitter output signals are multiplied by a square wave voltage signal generated by the quadrature oscillator 10 which is in phase with the voltage applied across the conductivity cell 14, to produce an output signal proportional to the real component of the current flowing through the conductivity cell 14, and thus proportional to the conductance G of the liquid.

In the second multiplier 28, the phase splitter signals are multiplied by a second square wave voltage signal, generated by the quadrature oscillator 10, which is 90° out-of-phase with the voltage applied across the conductivity cell 14, to produce an output signal proportional to the imaginary component of the current flowing through liquid in the conductivity cell 14, and thus proportional to the capacitance C of the liquid at its processing temperature T.

The liquid sensor probe 16 also includes a thermocouple 30 embedded in it, which produces a signal proportional to the temperature of the liquid at the probe 16. This temperature signal is amplified, and made linear with temperature in an amplifier and compensation circuit 32. This compensated temperature signal is directly proportional to the liquid process temperature T, and is utilized in the temperature compensation circuits of FIG. 2, together with a signal proportional to the reference temperature $T_o$, to convert the signals proportional to the conductance G and the capacitance C of the liquid at the measured temperature T to respective signals proportional to the conductance $G_o$ and the capacitance $C_o$ of the liquid at the reference temperature $T_o$. In most applications of this monitoring apparatus, the reference temperature $T_o$ is selected to be about the average temperature of the liquid during the processing operation, so that temperature compensation is only made over the range from the highest to the lowest temperature of the liquid during the processing operation.

Referring to FIG. 2, an amplifier 34 is used to produce a signal proportional to the reference temperature $T_o$, from which the signal proportional to the process liquid temperature T can be electrically subtracted. An input of the amplifier 34 is connected to a positive voltage source through the reference voltage resistor 36, and a feedback resistor 38 is connected between the input and the output of the amplifier 34 is directly proportional to the reference temperature $T_o$, the value of the reference temperature resistor 36 is inversely proportional to the reference temperature $T_o$, and can be a variable resistor, to allow selection of the reference temperature $T_o$. Also, since the output signal from the amplifier 34 must be equal to the output temperature signal from the thermocouple amplifier 32 at the selected temperature $T_o$, the value of the feedback resistor 38 is determined by the signal characteristics of the thermocouple amplifier 32. Assuming the voltage output signal of the thermocouple amplifier 32 is 10 volts at 500° C., and varies with the temperature T at a rate of 0.02 volts per degree C., the output voltage signal of the reference temperature amplifier 34 must be proportional to .02 ($- T_o$) volts. Thus, if the positive voltage source is 15 volts, and the value of the temperature resistance 36 is selected to equal $1/T_o \times 10^7$ ohms, the value of the feedback resistor 38 must be approximately 13,300 ohms (13.3 K) to produce an output signal of 0.02 ($- T_o$) volts.

This 0.02 ($- T_o$) voltage signal is supplied to an input of a summing amplifier 40 through a 10K resistor 42, and the 0.02 (T) voltage signal from the thermocouple amplifier 32 is also supplied to the same input of the amplifier 40 through another 10K resistor 44. A 100K feedback resistor 45 is connected between the input and the output of the amplifier 40, to produce an output temperature compensation signal of 0.2 ($T_o - T$) volts, which is supplied to both the conductance and capacitance compensation circuits. When the measured liquid temperature T is equal to the reference temperature $T_o$, there will be no temperature compensation signal.

This $0.2 (T_o - T)$ temperature compensation signal is supplied to an input of the amplifier 46 through a conductance compensation resistor 48, having a value of $1/b \times 10^2$ ohms, which may be a variable resistor to allow this apparatus to be used with different liquids having different "b" values. A 10K feedback resistor 50 connected between its input and output. The output of amplifier 46, representing $20b(T_o-T)$ is supplied to an input of summing amplifier 52 through a 200K scaling resistor 54.

The output signal from the first multiplier 26, which is proportional to the liquid conductance G, is supplied to the input of a log amplifier 58 through a resistor 60. Assuming that the maximum value of this conductance signal is + 5 volts full scale, the resistor 60 can be selected to have an ohmic value of 50K, to thus allow a maximum input current of 100μA to the log amplifier 58, and the log amplifier 58 selected to have a transfer function of $\mu$ log (Amperes input current/100μA), so that the voltage output of the log amplifier 58 will be − log G volts.

This − log G signal is also supplied to the input of the summing amplifier 52 through a 10K resistor 61, to produce an output signal of log G + b $(T_o-T)$ volts or log $G_o$ volts, since, as discussed earlier, log $G_o$ = log G + b $(T_o-T)$. This log $G_o$ voltage signal is supplied to an input of an amplifier 62 through a 10K resistor 64, and a 10K feedback resistor 66 is connected between this input and the output of the amplifier 62, to invert the input signal and produce an output signal from the amplifier 62 of − log $G_o$ volts. This − log $G_o$ signal is then supplied to the input of antilog amplifier 68 having a transfer function of $10 \times 10^{-x}$, where x is the input signal, to produce an output signal of 0 to 10 volts which is directly proportional to the conductance $G_o$ of the liquid.

In this embodiment, the maximum value of the capacitance signal from the second multiplier 28 is − 5 volts, and since a full scale positive output of 10 volts proportional to the capacitance $C_o$ of the liquid is desired, the input signal from the second multiplier 28 is shown as − C/2 volts.

The $0.2 (T_o - T)$ volt temperature compensation signal from the amplifier 40 is also supplied to an input of an amplifier 70 through a capacitance compensation resistor 72, having an ohmic value of $1/a \times 10^2$. This capacitance compensation resistor 72 can be a variable resistor, which can be adjusted for use with different liquids having different "a" values. A 5K amplifier feedback resistor 74 is connected between the input and the output of the amplifier 70, to produce an output signal of the amplifier 70 of $-10 [a (T_o - T)]$ volts, which is supplied to a first input of an analog multiplier 76. The −C/2 volt signal from the second multiplier 28 is supplied to a second input of the analog multiplier 76. The analog multiplier 76 has a transfer function of one-tenth of the product of the two input signals, to produce an output signal of a $(T_o - T)$ C/2 volts. This output signal of the analog multiplier 76 is supplied to an input of a summing amplifier 78 through a 10K resistor 80. The −C/2 volt signal from the second multiplier 28 is also supplied to the same input of the amplifier 78 through a 10K resistor 82. A 20K feedback resistor 84 is connected between the input and the output of the amplifier 78, to produce an output voltage signal proportional to $C - aC(T_o - T)$, or to the capacitance $C_o$ of the liquid, since, as discussed earlier, $C_o = C - aC(T_o - T)$.

In the preferred embodiment, the relatively high frequency of 1000 Hz was selected for the voltage applied across the electrodes of the conductivity cell to reduce the effects of charge transfer kinetics (Faradaic impedance) and electrode polarization, and to enhance the capacitive coupling of the electrodes with the liquid (double layer capacitance). Also, the operational amplifiers and other electronic components used in this apparatus are readily available commercially at this operating frequency. However, the invention is not limited to this frequency, any frequency within an approximate range of 100 Hz to $10^7$ Hz may be used. Also, the nominal operating temperature range, maximum deviation of the process temperature T from the reference temperature $T_o$, and the maximum absolute signal correction is determined by the choice of circuit components. For example, in the preferred embodiment the thermocouple 30 and other components of the process temperature measuring circuit and the reference temperature circuit were chosen for an operating temperature range of 0 - 500° C. and the components of the conductance temperature compensation circuit chosen for a maximum temperature deviation of plus or minus 50° C. and a maximum signal correction of 100% of the measured value. These ranges and limitations were only chosen because most applications of this apparatus fall within these ranges, and are not inherent limitations of the invention.

What is claimed is:

1. Monitoring apparatus for continuously determining at least one electrical characteristic of a liquid at a preselected reference temperature during processing of the liquid at a processing temperature which can vary from the reference temperature, which comprises:

probe means immersed in a liquid undergoing chemical processing for producing a current representing the electrical admittance of the liquid;

thermocouple means immersed in the liquid for producing a voltage representing the processing temperature of the liquid being monitored;

first signal resolution means connected to said probe means for producing, from said admittance current, a voltage representing the electrical conductance of the liquid at said processing temperature;

voltage generating means for producing a voltage corresponding to a reference temperature, said reference temperature voltage being equal and opposite to the processing temperature voltage produced by said thermocouple means when the reference temperature is equal to the processing temperature;

voltage summing means connected to said thermocouple means and to said voltage generating means for producing a temperature difference voltage representing the difference between said reference temperature voltage and said processing temperature voltage;

temperature compensation means connected to said summing means and to said first signal resolution means for modifying said voltage representing the conductance of the liquid at the processing temperature, to produce an output voltage representing the conductance of the liquid at the reference temperature.

2. A monitoring apparatus, as described in claim 1, which further comprises:
second signal resolution means connected to said probe means for producing, from said admittance current, a voltage representing the electrical capacitance of the liquid at said processing temperature; and
means for connecting said temperature compensation means to said second signal resolution means for modifying the processing temperature capacitance voltage with said temperature difference signal, to produce a voltage representing the capacitance of the liquid at the reference temperature.

3. A monitoring apparatus, as described in claim 2, wherein the probe means comprises:
a conductivity cell, immersed in the liquid;
energizing means connected to said conductivity cell for applying an alternating, sine wave voltage across the conductivity cell to produce a current therethrough which represents the electrical admittance of the liquid; and
transducer means connected to said conductivity cell for converting said current to said voltage representing the admittance of the liquid.

4. A monitoring apparatus, as described in claim 3 wherein the first and second signal resolution means comprises:
a quadrature oscillator means, which includes said energizing means, for producing a first alternating square wave voltage signal in phase with the sine wave voltage applied across the conductivity cell, and a second alternating square wave voltage signal which is 90° out-of-phase with said sine wave voltage;
phase splitter means connected to said transducer means for converting the admittance voltage produced by said transducer means into two equal and opposite voltages;
a first voltage multiplier means connected to said phase splitter means for multiplying one of the voltages produced by the phase splitter means by said first square wave voltage, to produce said voltage representing the electrical conductance of the liquid at the processing temperature; and
a second voltage multiplier means connected to said phase splitter means for multiplying the other of the voltage produced by said phase splitter means by the second square wave voltage signal, to produce said voltage representing the electrical capacitance of the liquid at the processing temperature within the conductivity cell.

5. A monitoring apparatus, as described in claim 4, wherein said thermocouple means includes a thermocouple which is mounted to the conductivity cell.

6. A monitoring apparatus, for use with a conductivity cell immersed in a liquid during processing of the liquid, for continuously determining at least one electrical characteristic of the liquid at a preselected reference temperature during processing of the liquid at a processing temperature which can vary from the reference temperature, which comprises:
thermocouple means immersed in a liquid undergoing chemical processing for producing a voltage representing the processing temperature of the liquid;
a conductivity cell immersed in said liquid;
energizing means connected to said conductivity cell for applying an alternating, sine wave voltage signal across the conductivity cell to produce a current therethrough which represents the electrical admittance of the liquid;
transducer means connected to said conductivity cell for converting said current to a voltage representing said electrical admittance of the liquid;
first voltage resolution means connected to said transducer means for producing, from said admittance voltage a voltage representing the electrical capacitance of the liquid at said processing temperature;
voltage generation means for producing a voltage corresponding to a reference temperature, said reference temperature voltage being equal and opposite to the processing temperature voltage produced by said thermocouple means when the reference temperature is equal to the processing temperature;
voltage summing means connected to said thermocouple means and to said voltage generating means for producing a temperature difference voltage representing the difference between the reference temperature voltage and the processing temperature voltage;
temperature compensation means connected to said summing means and to said first voltage resolution means for modifying said capacitance voltage produced by said first voltage resolution means in accordance with the temperature difference voltage produced by said voltage summing means, to produce a first output voltage representing the capacitance of the liquid at the reference temperature.

7. A monitoring apparatus, as described in claim 6, which further comprises:
second voltage resolution means connected to said transducer means for producing, from said admittance voltage, a voltage proportional to the electrical conductance of the liquid; and
means for connecting said temperature compensation means to said second voltage resolution means for modifying the conductance voltage produced by said second voltage resolution means with said temperature difference voltage produce by said voltage summing means, to produce a second output voltage representing the conductance of the liquid at said reference temperature.

* * * * *